(12) United States Patent
Filev et al.

(10) Patent No.: US 6,532,066 B1
(45) Date of Patent: Mar. 11, 2003

(54) VISION SYSTEM FOR IDENTIFICATION OF DEFECTS IN WET POLYMERIC COATINGS

(75) Inventors: Dimitar P. Filev, Novi, MI (US); Frank Migda, Commerce Township, MI (US); Gary Farquhar, Farmington Hills, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 215 days.

(21) Appl. No.: 09/634,616

(22) Filed: Aug. 5, 2000

(51) Int. Cl.$^7$ .............................................. G01N 21/00
(52) U.S. Cl. .................... 356/237.2; 356/600; 356/601; 356/237.1; 356/446; 348/92
(58) Field of Search .......................... 356/237.1, 237.3, 356/237.2, 446, 600; 382/108, 128

(56) References Cited

U.S. PATENT DOCUMENTS

| | | |
|---|---|---|
| 4,030,010 A | 6/1977 | Schwartz |
| 4,786,850 A | 11/1988 | Chmiel |
| 5,101,442 A * | 3/1992 | Amir ........................... 378/145 |
| 5,122,761 A | 6/1992 | Wischermann |
| 5,157,580 A | 10/1992 | Hegner et al. |
| 5,477,268 A * | 12/1995 | Shimbara et al. ........... 348/125 |
| 5,566,244 A | 10/1996 | Kato et al. |
| 5,726,705 A * | 3/1998 | Imanishi et al. ............... 348/92 |
| 5,801,965 A * | 9/1998 | Takagi et al. ............ 356/237.1 |
| 5,926,786 A | 7/1999 | McDonough et al. |

FOREIGN PATENT DOCUMENTS

| | | | |
|---|---|---|---|
| DE | 198 19 755 a1 | * | 11/1999 |
| JP | 11063959 | | 3/1999 |
| JP | 11072439 | | 3/1999 |

OTHER PUBLICATIONS

In re Burhans, 154 F.2d 690, 69 U.S.P.Q. 330, 33 C.C.P.A. 998 (Apr. 1, 1946).*
(Translation of German Patent Document) Dietz, DE 19819755 (Publication date: Nov. 11, 1999).*

* cited by examiner

Primary Examiner—Richard A. Rosenberger
Assistant Examiner—Vincent P. Barth
(74) Attorney, Agent, or Firm—Damian Porcari

(57) ABSTRACT

An apparatus and method of detecting defects or abnormalities in a wet polymeric surface coating of an object to limit or eliminate costs associated with retouching or reapplying the coatings on the object. The apparatus and method is accomplished by capturing an image of the wet coating surface of the object and comparing the image to known defect images to determine the type and location of the defect in the coating surface on the object. The coating application process can then be modified to remedy the coating application defect at the earliest possible instance.

12 Claims, 2 Drawing Sheets

VISION SYSTEM FOR IDENTIFICATION OF DEFECTS IN WET POLYMERIC COATINGS

TECHNICAL FIELD

The present invention relates to polymeric surface coatings and more particularly a method for identifying defects in wet polymeric surface coatings.

BACKGROUND

The process of applying polymeric surface coatings, such as automotive paints, to a surface is an important component in many manufacturing processes for both aesthetic and practical reasons. Polymeric coatings protect surfaces from degradation associated with physical conditions, such as light exposure or weather, while adding pleasing color or luster to visible surfaces.

Polymeric surface coatings can be applied in many different manners, including among others dipping, electrodeposition, and spraying. For most automotive applications, polymeric surface coatings are applied by spraying, with the coating being "cured", typically in an oven, in order to crosslink or harden the polymer components.

Application of polymeric surface coatings to surfaces is an inexact science. Defects in the coating caused by the application process are very common. Major defects can lead to premature coating failure, while minor defects may be unpleasing to the eye. Many of these defects are correctable by adjustments to application techniques, varying the composition of the coating or solvent delivery system, or adjusting the curing time or temperature. In this regard, it is important to discover the reasons why the defects are occurring in order to correct them as quickly as possible.

Many techniques are typically used to inspect surface coatings, from simple visual inspection to sophisticated surface measuring techniques. What is common among most of these techniques currently used is that they inspect dry, or cured, surface coatings. For example, U.S. Pat. No. 5,726,705 discloses an apparatus and method for inspecting defects or abnormalities of film by using a digitizing camera and light source.

One problem with inspecting cured coatings is determining where the problem causing the defect occurred. For instance, the problem could be caused by the spray equipment, the composition of the coating, or in the curing process. Another problem with inspecting cured coatings is that by the time the surface is inspected, a number of other parts may have already been coated with similar defects, and the cost to reapply or touch-up the surfaces is magnified by the number of parts that has been coated before the discovery of t he reason for the defect. For a production line for automobiles, for example, the number of units that could be affected may approach 100 units or more.

Thus, it is highly desirable to discover a defect in the wet surface coating at the earliest possible instance, as it limits the number of possible root causes of the surface defect, and further because it decreases the costs associated with reapplication or touching-up of parts by limiting the number of parts having the defect. This early discovery has the added benefit that any problems associated with curing will be limited to the curing mechanism or process, or due to the coating composition, and not due to the application of the coating. Another benefit of early discovery is that the sequencing of parts may be altered or adjusted to spray parts not being affected by the occurring defect. For example, if an automotive assembly line is having problems with red basecoats or with a particular paint bell atomizer, the assembly line may be sequenced to spray other colors or use other spray equipment until the root cause of the problem is remedied.

SUMMARY OF THE INVENTION

It is thus an object of the present invention to provide an apparatus and method for inspecting a wet (uncured) polymeric surface coating immediately after application so as to instantaneously observe defects, thus limiting or eliminating costs associated with retouch or reapplication.

The above object is accomplished by either digitizing an image in one of four vision systems (Specular Imaging, Directional Imaging, Patterned Imaging, or Diffused Light Imaging) of the wet polymeric surface with a digital camera or by scanning a polymeric surface with a laser sensor and scanner and comparing the produced images with known standards that indicate failures or passing surfaces.

One preferred method for visually inspecting a polymeric surface coating for defects or abnormalities comprises the steps of: capturing an image of the wet polymeric surface coating with a vision system and a detector system; digitizing the image; comparing the digitized image to a reference digitized image; and notifying the operator is the digitized image is a passing image or failing image due to a surface defect or abnormality.

Other objects and advantages of the present invention will become apparent upon considering the following detailed description and appended claims, and upon reference to the accompanying drawings.

DESCRIPTION OF THE PREFERRED EMBODIMENT(S)

Figure 1:
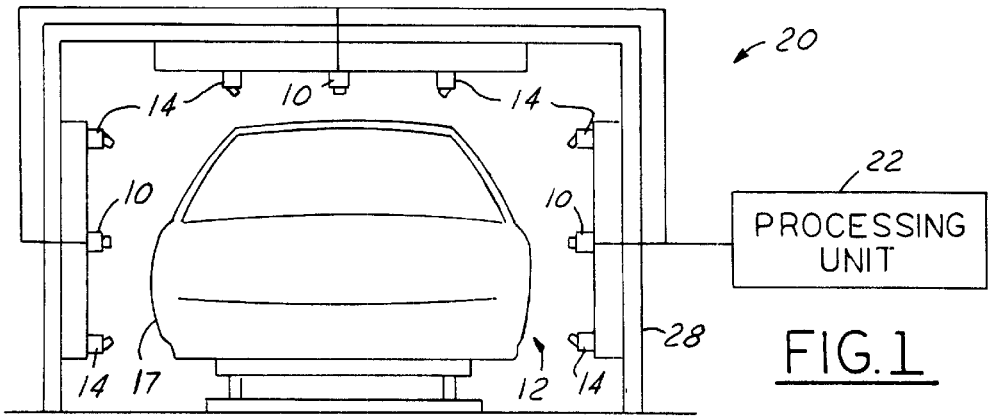
FIG. 1 is a schematic diagram showing one embodiment of a surface defect system in accordance with the invention.
Figure 2:
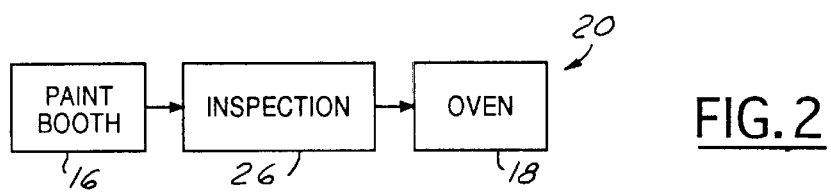
FIG. 2 is an illustration of a location of the surface defect inspection apparatus location on an assembly line.

With reference to the drawings, wherein like numerals refer to like parts in the several views, and in particular to FIGS. 1 and 2, there is shown a wet surface defect inspection apparatus 26 embodying the present invention. In FIG. 1, an object, in the illustrated case a vehicle body 12, having a wet polymeric surface coating 17 is placed on a carriage that transports the vehicle body 12 along an assembly line 20. A wet surface defect inspection apparatus 26 including a lighting unit 18, light detectors 10 and a processing unit 22, is placed along the assembly line between the painting equipment 16, where the vehicle body 12 has the wet polymeric surface coating 17 applied, and the curing oven 18, where the surface coating 17 is cured (crosslinked) into a dry film.

The lighting unit 28 has a plurality of light sources 14 positioned along the lighting unit 28. The light detectors 10 can be mounted on the lighting unit 28 or another member (not shown) and are connected to an processing unit 22, which processes and analyzes the signals gathered in the light detectors 10. The number of light detectors 10 may be varied to ensure that all points on the vehicle body 12 are sufficiently analyzed by the apparatus 26. Also, a number of various types of light sources 14 may be used.

Figure 3:
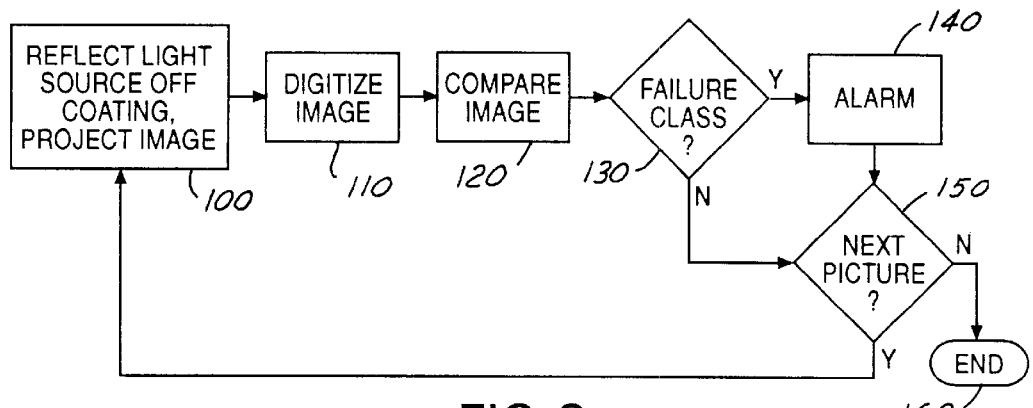
FIG. 3 is a logic flow diagram of a preferred embodiment of the present invention.

FIG. 3 represents a logic flow diagram for four possible embodiments of the present invention. In Step 100, a light source 14 is directed at a region of wet polymeric coating 17 on a vehicle body 12. The reflected light is imaged on a white screen (shown as 30 in FIGS. 4, 5, 6, and 7) and then captured by a detector 10. The image (shown as 32 in FIGS. 4, 5, 6, and 7) is then digitized by the processor 22 in Step 110. The digitized image is then compared to a set of reference digitized images in Step 120. The reference digitized images are prepared by capturing and digitizing an image of a known defect on a polymeric surface coating of like composition and properties (film thickness, color, etc.) as the coating to be analyzed in a similar manner to Steps 100, 110, and 120. Digitized images of reference samples without defects are also prepared. The reference digitized images are stored in the processor 22 and called when needed. The processor 22 then determines whether the digitized image is similar to a reference digitized image of a failure class in Step 130. If the digitized image is determined to be similar to that failure reference image, Step 140 notifies the operator of the type and location of the surface defect that has been detected. If the digitized image is not similar to a reference digitized image, Step 150 determines whether the entire vehicle has been scanned. If it has not, the process is reverted back to Step 100; otherwise the routine is completed in Step 160.

The area, or field of view, of the surface coating 17 that is being evaluated can be of any convenient size or shape. For example, images digitized experimentally using a specular vision system, as shown below in FIG. 4, could have a very large field of view (48 inches by 48 inches). Images digitized experimentally using a patterned lighting source, as shown below in FIG. 6, were limited to a much smaller field of view (up to 20 inches by 20 inches).

The surface defects referred to in Step 140 of FIG. 3 are defects that are commonly found in coating applications. One of the more common defects in coating objects is sagging, which results in drip marks or uneven coating distribution on vertical surfaces. Sagging is either caused by improper coating formulation or improper application techniques, both of which are correctable in most systems. Another common defect is dirt, which causes imperfections in the surface of coatings. Craters (sometimes referred to as fish eyes) are another problem in coatings and causes imperfections similar to dirt. Craters are typically formed when oils, such as machining oils, are accidentally introduced to coatings prior to application or are present on the object to be coated. Yet another surface defect is a thin paint area, which may cause the surface coating to have an uneven appearance and could affect the long term stability of the coating. Another common defect is spitting, in which paint is unevenly applied to a surface through the spraying equipment, such as a paint spray bell. Spitting can result from improper paint formulation or from improperly maintained or adjusted spraying equipment.

Each of these problems, as well as many others, can be identified in the wet polymeric surface coatings and indicate potential problems in the coating application process. The present invention is designed to indicate to the operator that these defects are present, so that the root causes of these defects may be remedied as quickly and efficiently as possible.

Figure 4:
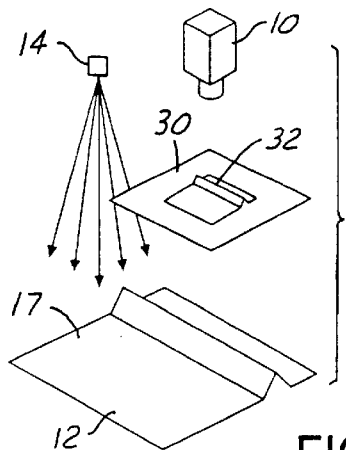
FIG. 4 is a schematic representation of Step 100 of FIG. 3, wherein the lighting source is a specular imaging lighting source.

FIGS. 4, 5, 6 and 7 refer to alternative light sources for use in Step 100 of FIG. 3. Referring to FIG. 4, the light source 14 is a specular imaging light source, or a light source originating from a point source of light. The specular light source 14 is mounted above the object 12 and the specular light source 14 is directed at the wet polymeric coating 17 of the object 12. A specular reflection off the wet polymeric coating surface 17 is imaged onto a white screen 30, and the image 32 is captured by a digital CCD camera 10.

Figure 5:
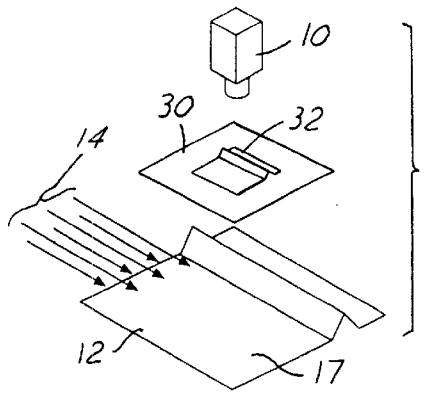
FIG. 5 is a schematic representation of Step 100 of FIG. 3, wherein the lighting source is a directional lighting source.

Referring to FIG. 5, the light source 14 is a directional lighting source. The directional lighting source 14 direct lights parallel to the wet polymeric surface 17 of the object 12 to be analyzed. Light is then reflected off of a defect in the wet polymeric surface coating 17 and imaged on a white screen 30. The image 32 is then captured by a CCD camera 10.

Figure 6:
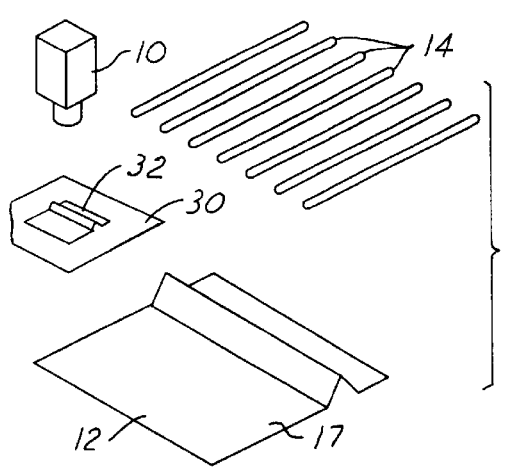
FIG. 6 is a schematic representation of Step 100 of FIG. 3, wherein the lighting source is a patterned lighting source.

Referring to FIG. 6, the light source 14 is a patterned lighting source. A patterned light source projects a known pattern on a flat, reflective surface, and imaging the reflection gives an indication of the flatness of the surface. Surface defects cause distortions in the imaged pattern. The patterned light source 14 is mounted above the object 12 and the patterned light source is directed at the wet polymeric surface. The reflected light is imaged on a white screen 30 and the image 32 is captured by a CCD camera.

Figure 7:
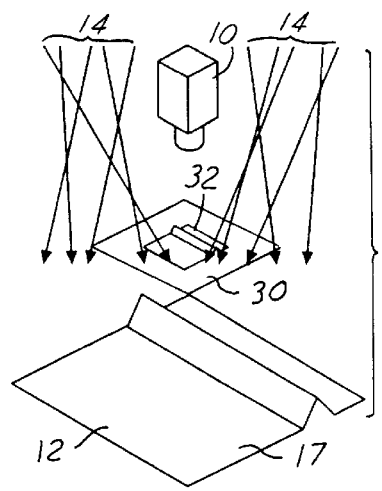
FIG. 7 is a schematic representation of Step 100 of FIG. 3, wherein the lighting source is a diffuse lighting source.

Referring to FIG. 7, the light source 14 is a diffuse light source. The diffuse light source is mounted above or along side an object 12 sample and the light is directed at the sample. The reflected light is imaged on a white screen 30 and the image 32 is captured by a CCD camera.

Diffuse front lighting minimizes shadows and specular reflection for a uniform surface background. This approach reduces "noise" typically induced by an orange peel surface while illuminating large features such as holes and character lines. Using such a method, however, may eliminate detection of subtle defects, such as sags. Images obtained via diffuse lighting can be used as references to identify desired features and distinguish those desired features from defects.

Figure 8:
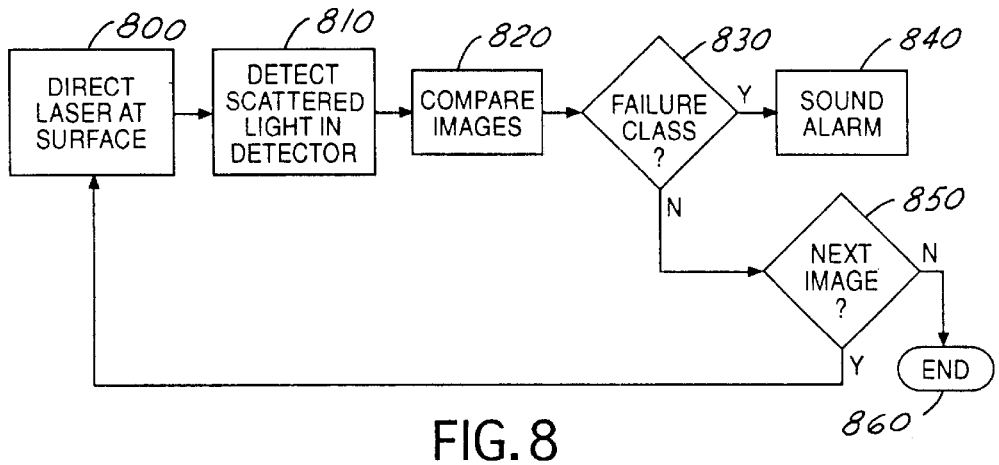
FIG. 8 is a logic flow diagram of another preferred embodiment of the present invention.

FIG. 8 represents a logic flow diagram for another preferred embodiment of the present invention, where a laser scanner replaces the visual light source and a scattered light detector replaces the light detector (the CCD camera in embodiments of FIGS. 4, 5, 6 and 7). A more detailed explanation of this embodiment is explained below in FIG. 9. In Step 800, a laser beam is directed at the wet polymeric surface through a series of mirrors. As the laser beam passes over the defect in the paint surface, the distribution of scattered light detected by a scattered light detector changes. In Step 810, the scattered light detector captures the change in scattered light and produces an image. In Step 820, the image is digitized. The digitized image is then compared to known reference defect images by a processor in Step 830. If the digitized image is determined to be similar to a reference defect image, Step 840 notifies the operator of the type of defect detected and the location of the defect and proceeds to Step 850. If the digitized image is not similar, Step 850 determines whether the entire object has been scanned. If the image has not been scanned, return to Step 800, otherwise end the diagnostic in Step 860 and report the results.

Figure 9:
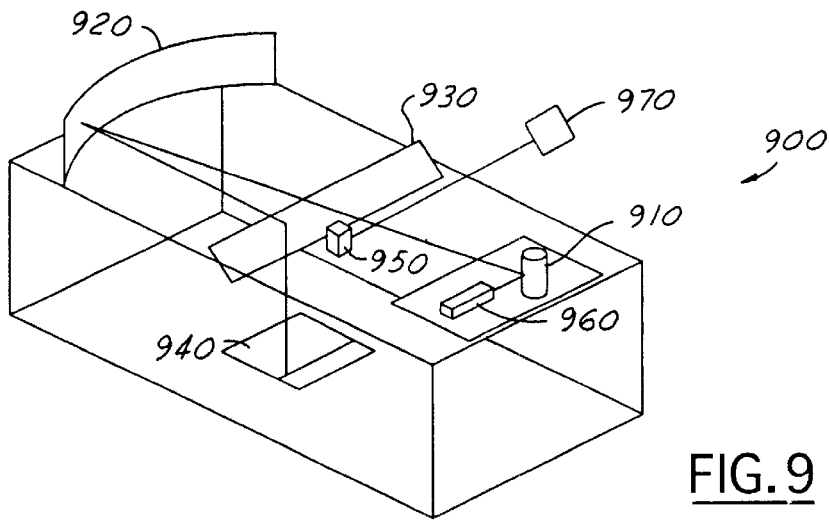
FIG. 9 is a schematic representation of Step 800 of FIG. 8.

FIG. 9 is a schematic diagram of the laser scanning wet polymeric surface defect detection apparatus 900 which is another embodiment of the present invention. The apparatus 900 comprises a laser 960, a scanning mirror 910, a telecentric mirror 920, a fold mirror 930, an object 940 having a wet polymeric surface 945, a scattered light detector 950, and a processing unit 970. The laser 960 directs a laser beam that is reflected by the scanning mirror 910, the telecentric mirror 920, and the fold mirror 930 towards the object 940. Laser light is then reflected off the wet polymeric surface 945 and is detected by the scattered light detector 950. When a surface defect appears on the wet surface 945, the distribution of scattered light will change, and the defect will be captured by the scattered light detector 950. The processing unit 970, typically microprocessor based, will digitize an image of the defect and compare the image to known reference defect digitized images stored in the processing unit 970. If the defect is similar to a known defect, such as a sag or a crater, the processing unit 970 will notify the operator of the type and location of the defect.

Experimental sag testing of the five preferred embodiments described in FIGS. 4, 5, 6, 7 and 9 above indicate that the specular lighting system embodiment of FIG. 4 was particularly adept at detecting sag defects as small as one-eighth of an inch. Further, the directional lighting system of FIG. 5 was adept at detecting sag defects as small as one-half of an inch, and the diffuse lighting system of FIG. 7 enhances the performance of the directional system by providing higher contrast at defect sites.

Thus, the present invention provides a quick and easy way to detect defects in wet polymeric surface coatings at the earliest possible instance after application. By giving feedback at the earliest possible instance, modifications may be made to application equipment or coating composition before many parts have been coated. This will limit or eliminate costs for associated with retouching or reapplying coatings.

Further, by identifying trouble spots on coating surfaces likely to have defects, such as sagging, the number of readings necessary for detecting problems may be reduced, leading to additional cost savings associated with implementing the present invention or for observing defects after an oven curing process.

While it is contemplated that the present invention may be used in industrial applications where a large number of parts may be coated, such as an automotive assembly line, it is apparent that the present invention may be useful in any application where surfaces are inspected, such as in the furniture industry.

While the invention has been described in terms of preferred embodiments, it will be understood, of course, that the invention is not limited thereto since modifications may be made by those skilled in the art, particularly in light of the foregoing teachings.

What is claimed is:

1. A method for visually inspecting a wet polymeric surface coating for defects or abnormalities, the method comprising the steps of:
    capturing an image of the wet polymeric surface coating with a vision system and a detector system;
    digitizing said image into a digitized image;
    comparing said digitized image to a reference digitized failure image;
    classifying said digitized image as a failure image when said digitized image is similar to said reference digitized failure image; and
    notifying an operator when said digitized image is a failure image.

2. A method according to claim 1, wherein the step of capturing an image comprises the step of capturing an image of the wet polymeric surface coating with a diffuse lighting imaging system and a digital camera.

3. A method according to claim 1, wherein the step of classifying said digitized image as a failure image comprises the steps of:
    determining whether said digitized image has a defect; and
    classifying said digitized image as a failure image when said digitized image is determined to have said defect.

4. The method according to claim 3, wherein the step of determining whether said digitized image has a defect comprises the step of determining whether said digitized image has a defect selected from a group consisting of a sag defect, a crater defect, a dirt defect, a thin paint defect or a spitting defect.

5. A method as in claim 1, wherein the step of capturing an image comprises the step of capturing an image of the wet polymeric surface coating using a laser scanning vision system and a scattered light detector system.

6. An apparatus for inspecting surface defects in a wet polymeric surface coating, the apparatus comprising:
    a vision system for illuminating the wet polymeric surface coating;
    a detector system for capturing an image from said wet polymeric surface coating; and
    an analyzer system for digitizing said image and for reading and comparing said digitized image to a series of reference digitized images.

7. An apparatus as in claim 6, wherein said vision system is a scanning laser vision system.

8. An apparatus as in claim 6, wherein said detector system comprises a digital camera.

9. An apparatus as in claim 6, wherein said analyzer system comprises a microprocessor-based analyzer system.

10. An apparatus as in claim 7, wherein said detector system is a scattered light detector.

11. An apparatus as in claim 9, wherein said series of reference images comprises a reference sag image, a reference crater image, a reference thin paint image, a reference spitting image, and a reference dirt image.

12. An apparatus as in claim 8, wherein said digital camera is a CCD camera.

* * * * *